United States Patent
Bykovskaia et al.

(10) Patent No.: US 9,192,628 B2
(45) Date of Patent: Nov. 24, 2015

(54) TREATMENT METHOD FOR RELAPSING-REMITTING MULTIPLE SCLEROSIS

(71) Applicant: Regenex LLC, Moscow (RU)

(72) Inventors: Svetlana Nunevna Bykovskaia, Moscow (RU); Daria Dmitrievna Eliseeva, Moscow (RU); Igor Alekseevich Zavalishin, Dedovsk (RU)

(73) Assignee: REGENEX LLC, Odintsovo (RU)

( * ) Notice: Subject to any disclaimer, the term of this patent is extended or adjusted under 35 U.S.C. 154(b) by 0 days.

(21) Appl. No.: 14/186,115

(22) Filed: Feb. 21, 2014

(65) Prior Publication Data

US 2014/0170176 A1 Jun. 19, 2014

Related U.S. Application Data

(63) Continuation of application No. 13/768,321, filed on Feb. 15, 2013, now Pat. No. 8,697,060.

(51) Int. Cl.
- *A61K 35/14* (2015.01)
- *A61K 35/17* (2015.01)
- *C12N 5/0783* (2010.01)

(52) U.S. Cl.
CPC ............ *A61K 35/17* (2013.01); *C12N 5/0637* (2013.01); *C12N 2501/15* (2013.01); *C12N 2501/2302* (2013.01); *C12N 2501/505* (2013.01); *C12N 2501/51* (2013.01); *C12N 2501/515* (2013.01)

(58) Field of Classification Search
CPC ....................................................... A61K 35/17
See application file for complete search history.

(56) References Cited

U.S. PATENT DOCUMENTS

2011/0014697 A1* 1/2011 Roetzschke et al. ....... 435/372.3

FOREIGN PATENT DOCUMENTS

WO 2009/062260 A1 5/2009

OTHER PUBLICATIONS

Antonetti et al. (2002) "A comparison of the biologic activity of two recombinant IFN-beta preparations used in the treatment of relapsing-remitting multiple sclerosis," J. Interferon & Cytokine Res. 22:1181-1184.
Borsellino et al. (2007) "Expression of ectonucleotidase CD39 by Foxp3+ Treg cells: hydrolysis of extracellular ATP and immune suppression," Blood 110(4):1225-1232.
Brunstein et al. (2011) "Infusion of ex vivo expanded T regulatory cells in adults transplanted with umbilical cord blood: safety profile and detection kinetics," Blood 117(3):1061-1070.
Weissert (2011) "Progressive multifocal leukoencephalopathy," J. Neuroimmunol. 231:73-77.
Chofflon (2005) "Mechansims of action for treatments in multiple sclerosis: Does a heterogeneous disease demand a multi-targeted therapeutic approach?" Biodrugs 19(5):299-308.
Comabella et al. (2012) "Immunopathogenesis of multiple sclerosis," Clin. Immunol. 142:2-8.
Davidson et al. (2001) "Autoimmune diseases," N. Engl. J. Med. 345(5):340-350.
Dejaco et al. (2005) "Imbalance of regulatory T cells in human autoimmune diseases," Immunol. 117:289-300.
Di Ianni et al. (2011) "Tregs prevent GVHD and promote immune reconstitution in HLA-haploidentical transplantation," Blood 117(14):3921-3928.
European Medicines Agency (2010) "Questions and answers on the review of Tysabri (natalizumab): Outcome of a procedure under Article 20 of Regulation (EC) No. 726/2004," http://www.emea.europa.eu/docs/en_GB/document_library/Medicine_QA/2010/01/WC500070009.pdf, 1-3.
Frisullo et al. (2008) "Regulatory T cells fail to suppress CD4+ T-bet+ T cells in relapsing multiple sclerosis patients," Immunol. 127:418-428.
Goodin, et al. (2002) "Disease modifying therapies in multiple sclerosis: Report of the therapeutics and technology assessment subcommittee of the American Academy of Neurology and The MS Council for Clinical Practice Guidelines," Neurol. 58:169-178.
Hartung (2009) "High-dose, high-frequency recombinant interferon beta-1a in the treatment of multiple sclerosis," Expert Opin. Pharmacother. 10(2):291-309.
Haas et al. (2007), "Prevalence of newly generated naive regulatory T cells (Treg) is critical for Treg suppressive function and determines Treg dysfunction in multiple sclerosis," J. Immunol.179:1322-1330.
Hall et al. (1990) "Specific unresponsiveness in rats with prolonged cardiac allograft survival after treatment with cyclosporine: III. Further characterization of the CD4+ suppressor cell and its mechanisms of action," J. Exp. Med. 171:141-157.
Huan et al. (2005) "Decreased FOXP3 levels in multiple sclerosis patients," J. Neurosci. Res. 81:45-52.
Huynh et al. (1995) "Interferon-β downregulates interferon-γ-induced class II MHC molecule expression and morphological changes in primary cultures of human brain microvessel endothelial cells," J. Neuroimmunol. 60:63-73.
Issa et al. (2012) Translating tolerogenic therapies to the clinic—where do we stand? Front. Immunol. 3(254):1-14.
Kappos et al. (2005) "Neutralizing antibodies and efficacy of interferon β-1a: A 4-year controlled study" Neurol. 65:40-47.
Kieseier et al. (2010) "Chemotherapeutics in the treatment of multiple sclerosis," Ther. Adv. Neurol. Disord. 3(5):277-291.
Lebrun et al. (2011) "Cutaneous side-effects of immunomodulators in MS," Int. J. Mult. Scler. 17(3):88-94.

(Continued)

*Primary Examiner* — John Ulm
(74) *Attorney, Agent, or Firm* — Ann-Louise Kerner; DLA Piper LLP (US)

(57) ABSTRACT

Disclosed is a method for treating relapsing-remitting multiple sclerosis in a patient by administering to the patient autologous, ex vivo-expanded $CD4^+CD25^+Foxp3^+CD127^{low}$ T reg cells when the patient is in remission. Also disclosed is a method of inhibiting the activity of autoimmune, autologous cytotoxic T and B cells in a patient suffering from relapsing-remitting multiple sclerosis, comprising administering a therapeutically effective amount of autologous $CD4^+CD25^+Foxp3^+CD127^{low}$ T reg cells to the patient.

8 Claims, 10 Drawing Sheets

(56) References Cited

OTHER PUBLICATIONS

Leppert et al. (1996) "Interferon beta-1b inhibits gelatinase secretion and in vitro migration of human T cells: A possible mechanism for treatment efficacy in multiple sclerosis," Ann. Neurol. 40(6):846-852.
Liu et al. (2001) "Immunomodulatory effects of interferon beta-1a in multiple sclerosis," J. Neuroimmunol. 112:153-162.
Neuhaus et al. (2001) "Mechanisms of action of glatiramer acetate in multiple sclerosis," Neurol. 56:702-708.
Noseworthy et al. (2000) "Multiple sclerosis," N. Engl. J. Med. 343(13):938-952.
Reder (2007) "Neutralizing antibodies in multiple sclerosis: a complex impact on interferon responses, magnetic resonance imaging findings and clinical outcomes," Mult. Scler. 13:S53-S62.
Sakaguchi et al. (1995) "Immunologic self-tolerance maintained by activated T cells expressing IL-2 receptor α-chains (CD25): Breakdown of a single mechanism of self-tolerance causes various autoimmune diseases," J. Immunol. 155:1151-1164.
Saresella et al. (2008) "CD4+ CD25+ FoxP3+ PD1—regulatory T cells in acute and stable relapsing-remitting multiple sclerosis and their modulation by therapy," FASEB J. 22:3500-3508.
Schreiner et al. (2004) "Interferon-β enhances monocyte and dendritic cell expression of B7-H1 (PD-L1), a strong inhibitor of autologous T-cell activation: relevance for the immune modulatory effect in multiple sclerosis," J. Neuroimmunol. 155(1-2):172-182.
Tischner et al. (2007) "Glucocorticoids in the control of neuroinflammation," Mol. & Cell. Endocrinol. 275:62-70.
Trzonkowski et al. (2009) "First-in-man clinical results of the treatment of patients with graft versus host disease with human ex vivo expanded CD4+ CD25+ CD127—T regulatory cells," Clin. Immunol. 133:22-26.
Venken et al. (2008) "Natural naive CD4+ CD25+ CD127low regulatory T cells (Treg) development and function are in multiple sclerosis patients: Recovery of memory Treg homeostasis during disease progression," J. Immunol. 180:6411-6420.
Venken et al. (2007) "Compromised CD4+ CD25high regulatory T-cell function in patients with relapsing-remitting multiple sclerosis is correlated with a reduced frequency of FOXP3-positive cells and reduced FOXP3 expression at the single-cell level," Immunol. 123:79-89.
Viglietta et al. (2004) "Loss of functional suppression by CD4+ CD25+ regulatory T cells in patients with multiple sclerosis," J. Exp. Med. 199(7):971-979.
Von Andrian et al. (2003) "α4 integrins as therapeutic targets in autoimmune disease," N. Engl. J. Med. 348(1): 68-72.
Weinstock-Guttman et al. (2004) "Risk of bone loss in men with multiple sclerosis," Mult. Scler. 10:170-175.
Mikol et al. (2007) "The Regard trial: a randomised assessor-blinded trial comparing interferon beta-1a and glatiramer acetate in relapsing-remitting multiple sclerosis," 23rd Congress of the European Committee for the Treatment and Research in Multiple Sclerosis (ECTRIMS) and 12th Annual Conference of Rehabilitation in MS (RIMS), Prague, Czech Republic. Poster 110 Svetlana.
Menge et al. (2008) "Disease-modifying agents for multiple sclerosis," Drugs 68(17):2445-2468.
McCormack et al. (2004) "Interferon-beta-1b: a review of its use in relapsing-remitting and secondary progressive multiple sclerosis," CNS Drugs 18(8):521-546.
Lyssuk et al. (2007) "Reduced number and function of CD4+ CD25high Foxp3 regulatory T cells in patient with systemic lupus erythematosus," Adv. Exper. Med. Biol. 601:113-119.
International Search Report and Written Opinion, PCT/RU2013/000119, dated Sep. 5, 2013, 7 pages.
Bykovskaya et al. (2013) "CD4+CD2s+ FOXPJ+ T Regulatory Cell Analysis in Autoimmune Diseases," Russian National Research Medical University, 3:20-28 (Russian).
Merkuluv (2010) "Axonopathy in the pathogenesis of multiple sclerosis, peripheral diffuse and local motor neuropathies . . . " J. Neurol. Psychiatry 110:8:4 (Russian).
Zavalishin et al. (2003) "Results of a multicenter study of Rebif-22 mcg administration in Russia" Nevrol Psikhiatr Im S S Korsakova (Spec No. 2):73-8 (Russian).
Zavalishin et al. (2003) Multiple sclerosis: etiology and pathogenesis Zh Nevrol Psikhiatr Im S S Korsakova (Spec No. 2):10-7 (Russian).
Musaeva et al (2003) Pyramidal syndrome in lateral amyotrophic sclerosis: clinico-morphological analysis Zh Nevrol Psikhiatr Im S S Korsakova 103(5):19-25 (Russian).

\* cited by examiner

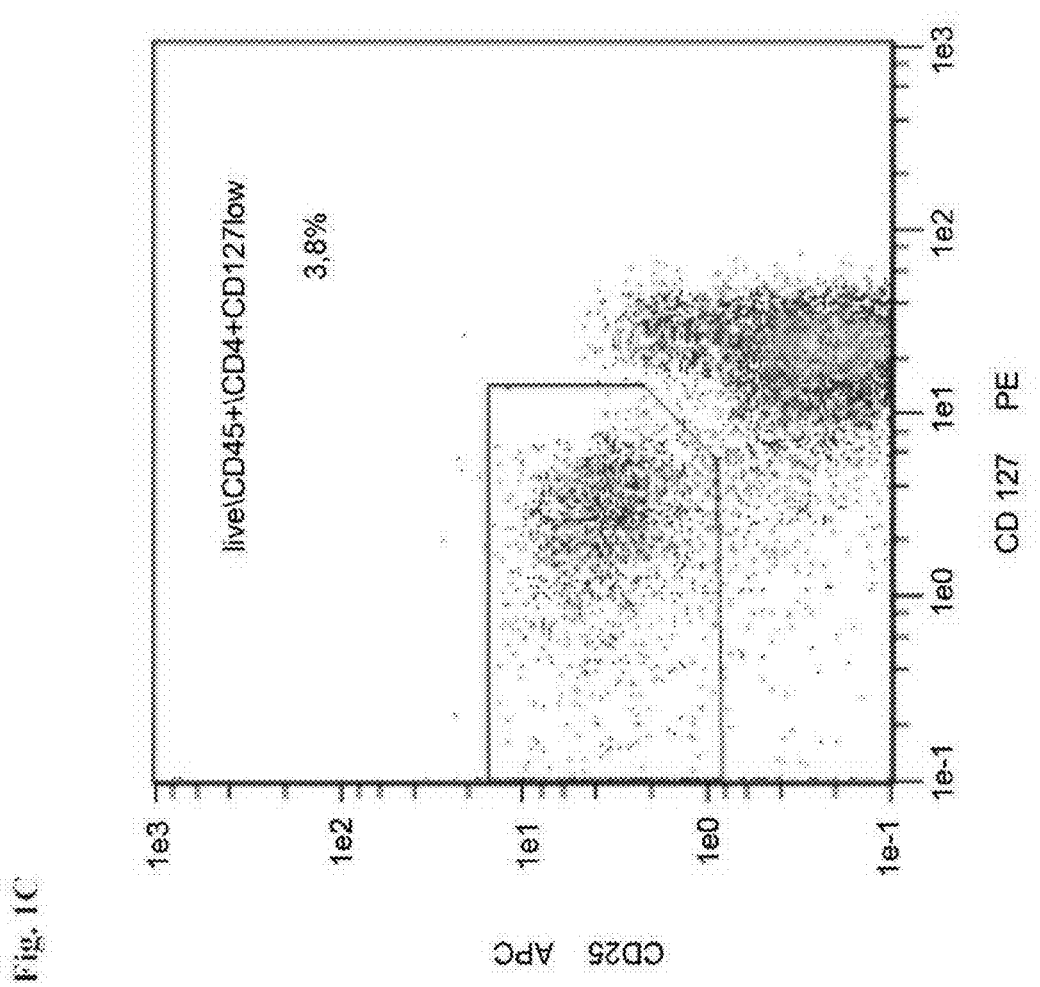

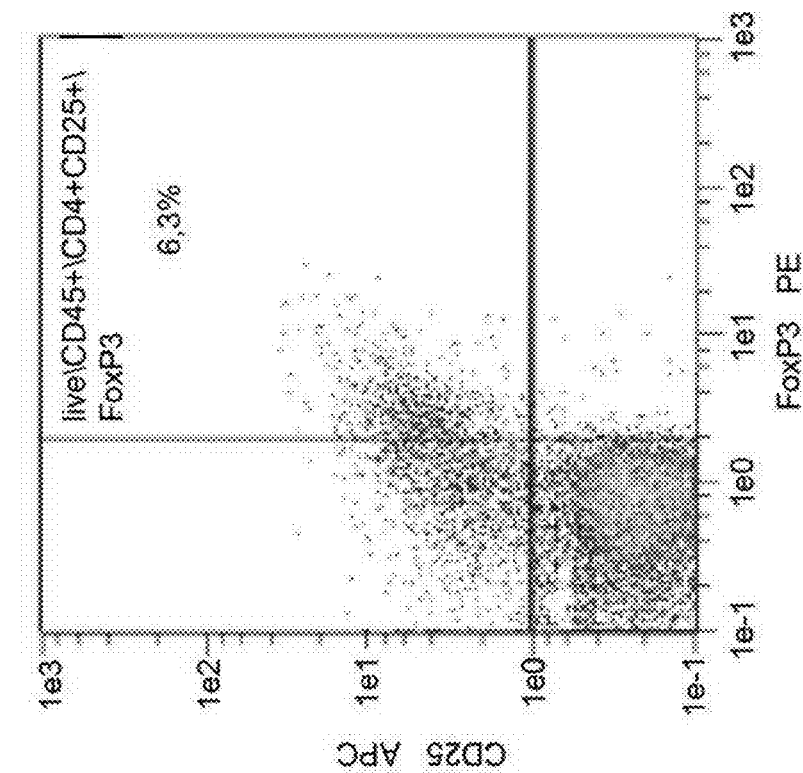
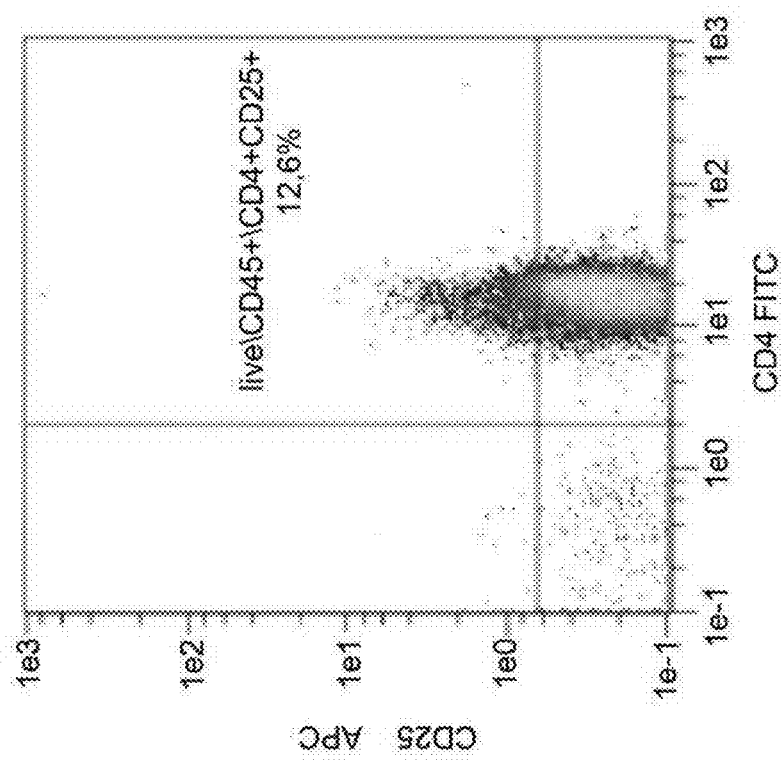
Fig. 2B
Fig. 2A

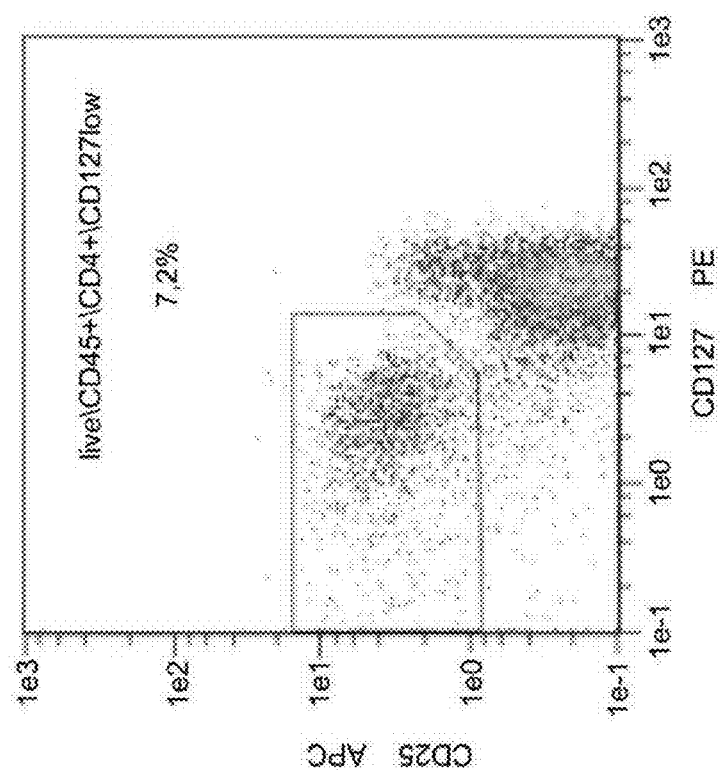

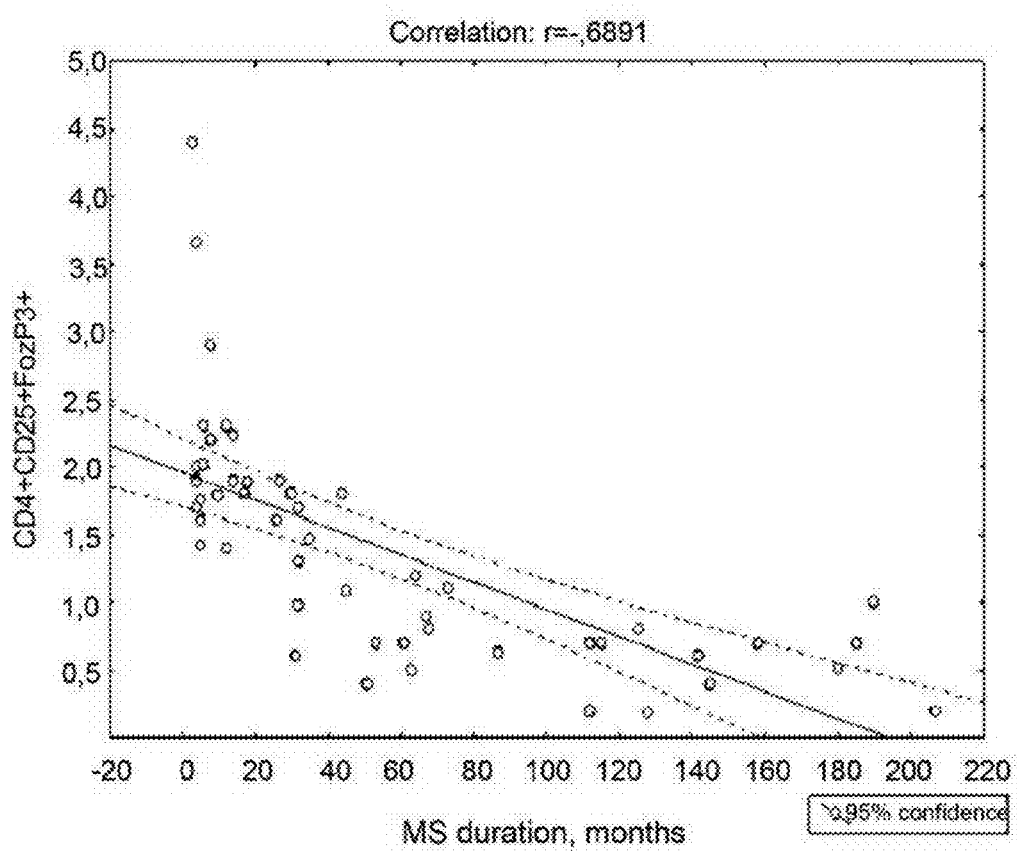

TREATMENT METHOD FOR RELAPSING-REMITTING MULTIPLE SCLEROSIS

CROSS-REFERENCE TO RELATED APPLICATION

This application is a continuation of U.S. application Ser. No. 13/768,321, entitled "Treatment Method for Relapsing-Remitting Multiple Sclerosis," which was filed on Feb. 15, 2013, which is a continuation-in-part of Russian Patent Application No. 2012127158/20(042109) entitled "Method of Treatment for Remitting Relapsing Multiple Sclerosis," which was filed on Jun. 29, 2012. The entirety of the aforementioned applications is herein incorporated by reference.

FIELD OF INVENTION

The invention relates to medicine, pharmacology, and cell biotechnology, and more specifically to the treatment of relapsing-remitting multiple sclerosis (relapsing-remitting MS).

BACKGROUND

Multiple sclerosis (MS) is a chronic, progressive disease of the central nervous system (CNS), which is clinically manifested by multisystemic neurological symptoms and signs, and is pathomorphologically characterized by formation of multiple foci of demyelination in the white matter of the brain and spinal cord (Noseworthy et al. (2000) *New Engl. J. Med.* 343:938-952). The pathogenetic mechanism of the disease is the activation of autoreactive T cells specifically against components of the myelin, which leads to damage of the myelin sheath of oligodendrocytes and axons and consequently to formation of a persistent neurological deficit in the patient (Comabella et al. (2012) *Clin. Immunol.* 142:2-8).

Today, drugs used for MS drug therapy can be divided into two groups: drugs for symptomatic treatments, and drugs modifying the course of multiple sclerosis (Goodin, et al. (2002) *Neurol.* 58:169-178; Menge et al. (2008) *Drugs* 68:2445-2468). Drugs used for symptomatic treatment of MS include glucocorticoids (e.g., prednisolone, metypred, Solu-Medrol) and immuno-suppressive drugs (e.g., cyclophosphan, azathioprine, and mitoxantrone).

The mechanisms of action of glucocorticoids include both a reduction in the number of activated immunocompetent cells and inhibition of autoantibodies (Tischner et al. (2007) *Mol. Cell. Endrocrinol.* 275:62-70). The anti-inflammatory effect results in the reduction of the permeability of the blood vessels and the blood-brain barrier, which, in turn, leads to a reduction in the rate of prostaglandin synthesis. Due to reduced permeability of the endothelium of the capillaries, migration of leukocytes and other cells to the inflammatory focus is reduced. Adrenocorticotropic hormone (ACTH) and its synthetic analogs (tetracosactide) have a neurotransmitter effect.

A disadvantage of this group of drugs is the symptomatic nature of the treatment, where the prolonged use of these drugs causes hypercorticism syndrome (Cushing's syndrome), psychiatric disorders, arterial hypertension, and hypertrichosis (Weinstock-Guttman et al. (2004) *Multiple Sclerosis* 10:170-175).

Along with corticosteroids, drugs used in primary or secondary progressive multiple sclerosis include cytostatics, such as azathiaprine, cladribine, methotrexate, cyclophosphamide, mitoxatrone, etc. These drugs have pronounced side effects associated with poor tolerability and depression of bone marrow hemopoiesis.

Pathogenetic treatment of MS includes the use of a number of drugs, such as interferon beta ($IFN_\beta$)-1a and $IFN_\beta$-1b. The therapeutic effects of $IFN_\beta$ are associated with the inhibition of antigen presentation and suppression of both the proliferation and the activation of inflammatory cells. IFN-β1 induces anti-inflammatory cytokines and a change in the cytokine profile toward the anti-inflammatory phenotype, and also reduces entry of leukocytes into the central nervous system through the blood-brain barrier (see, e.g., Chofflon (2005) *Biodrugs* 19:299-308; Schreiner et al. (2004) *J. Neuroimmunol.* 155:172-182; Leppert et al. (1996) *Ann. Neurol.* 40:846-852; Finocchiaro et al. (2002) *J. Interferon Cytokine Res.* 22:1181-1184; Huynh et al. (1995) *J. Neuroimmunol.* 60:63-73; Liu et al. (2001) *J. Neuroimmunol.* 112:153-162.

The major disadvantages of $IFN_\beta$ use are the length of treatment (at least six months, and if a positive effect is observed, potentially lifelong), the high cost of a treatment course, and the side effects, including flu-like symptoms (elevated body temperature, acute muscle and joint pain, weakness, fatigue), as well as the production of neutralizing antibodies. In most patients, these antibodies appear between 6 and 18 months after beginning treatment. The negative effect of neutralizing antibodies has been proven by clinical parameters (frequency of relapse) and by neurovisualization parameters of MS activity, as well as by the progression of disability (Kappos (2005) *Neurol.* 65:40 and Reder (2007) *J. Multiple Sclerosis* 13:53-62).

Another drug used for treatment of multiple sclerosis is glatiramer acetate (Copaxone), a synthetic polymer of four amino acids. The mechanism of this drug involves competitive binding with the major histocompatibility complex class II molecule, participating in presentation of antigens with the major myelin protein. This drug also activates Th2 $CD4^+$ T cells crossing the blood-brain barrier and induces suppression of the autoimmune response against multiple myelin antigens (Neuhaus et al. (2001) *Neurol.* 56:702-708).

Direct comparative studies of Copaxone with high doses of beta interferons (Refib, Betaferon) have not shown any significant differences in the ability of the drugs to reduce the relapse frequency, or to reduce the number and volume of lesions on MRI (Mikol et al. (2007) Program and Abstracts of the ECTRIMS: 23rd Congress of the European Committee for Treatment and Research in Multiple Sclerosis, Oct. 11-14, 2007, Prague, Czech Republic, Poster 119). The disadvantages of treatment with this drug include the need for prolonged use (course of treatment lasts at least 6 months), the high cost, and the presence of side effects both at the injection sites (hyperemia, stinging) and a generalized post-injection reaction (breathlessness, tachycardia, flushed skin, cold sweats, chest pain, and dimming of vision). Furthermore, when the drug is taken for many years, lipoatrophic changes may occur (local atrophy of fatty tissue at the injection sites) (Lebrun et al. (2011) *J. Multiple Sclerosis* 17:88-94).

Also used for MS treatment is Natalizumab (Tysabri), a preparation of monoclonal antibodies against integrin molecules. In MS patients, the drug blocks molecular interaction between a4-integrin (which can be expressed on autoaggressive lymphocytes), and vascular cell adhesion molecule 1 (VCAM-1) of the vascular endothelium of the blood-brain barrier, and prevents the migration of lymphocytes through the endothelium to the inflammatory foci in the CNS (Von Andrian et al. (2003) *New Engl. J. Med.* 348:68-72).

The disadvantages of the drug include high frequency (in up to 25% of patients) of side effects (headaches, dizziness, itching, chills, hives, asthenia). Delayed side effects are associated with immunosuppression arising as a result of the action of the drug, which include urinary tract infections, vaginal infections, pneumonia, tonsillitis, and herpes infection. 0.1% of the patients who undergo treatment with Natalizumab develop liver, and accordingly, the European Medicines Agency for registration of drugs (EMA) has recommended routine monitoring of patients with liver damage. However, the most serious side effect of Tysabri treatment is progressive multifocal leukoencephalopathy (PML), a demyelinating disease manifested by headaches, paresis, loss of coordination, vision impairment, speech impairment (aphasia) and pronounced cognitive deficits. Most often, the disease ends with the death of the patient. PML is associated with activation (under immunodeficiency conditions) of the JCV polyomavirus in the CNS.

Thus, what is needed is an improved and efficacious treatment for relapsing-remitting MS with reduced or no side effects.

SUMMARY

It has been discovered that there is an inverse relationship between the number of T reg cells in the peripheral blood of patients with relapsing-remitting MS and the degree of disability and severity of the disease. These discoveries have been exploited to develop the present method of treating of relapsing-remitting MS. Administering autologous, ex vivo-expanded —$CD4^+CD25^+Foxp3^+CD127^{low}$ regulatory T (T reg) cells during the remission phase lowers the level of autoimmune activity of certain T cells, thereby reducing symptoms and maintaining the remission phase indefinitely or for at least longer periods of time than what is seen on average without treatment.

In one aspect, the disclosure provides a method of preventing or treating relapsing-remitting MS in a patient in need thereof, comprising: administering a therapeutically effective amount of autologous T reg cells to the patient during the remission phase.

In some embodiments, the administering step comprises administering the therapeutically effective amount of autologous T reg cells more than one time at the start of treatment to increase the number of T reg cells in patient's blood to a number comparable to number in the blood of healthy donors. In some embodiments, the administering step comprises administering a therapeutically effect amount of T reg cells about 1 to 7 times at the start of treatment.

In some embodiments the method further comprising measuring the number of T reg cells in the blood of the patient before and after each administering step. In particular embodiments, the number of T reg cells in a patient's blood is measured monthly, or every 1 to 3 months, or every 2 to 3 months, after the initial administering step.

In particular embodiments, the method further comprises a second administering step if the number of T reg cells measured in the blood of a patient after the first administering step is less than the number of T reg levels in blood of a healthy donor.

In some embodiments, the autologous T reg cells administered are expanded ex vivo before they are administered to the patient. In certain embodiments, the number of autologous T reg cells administered at one time is about $1\times10^6$ to about $1.1\times10^7$ per kg body weight to the patient. In many embodiments, the autologous T reg cells are administered by subcutaneous, intravenous, and/or intramuscular injection.

Also provided by the present disclosure is a method of inhibiting the activity of autoimmune, autologous, cytotoxic T and B cells in a patient suffering from relapsing-remitting MS, comprising: administering a therapeutically effective amount of autologous T reg cells to the patient. In some embodiments, the administering step is performed more than one time throughout the life of the patient. In certain embodiments, the administering step is performed every 1 to 7, 2 to 6, 3 to 6, or 4 to 5 months after the first administering step. In many embodiments, the administering step comprises administering about $1\times10^6$ to about $1.1\times10^7$ autologous T reg cells per kg body weight to the patient. In many embodiments, the autologous T reg cells are administered by subcutaneous, intravenous, and/or intramuscular injection. In some embodiments, the autologous T reg cells administered are expanded ex vivo before they are administered to the patient.

DESCRIPTION OF THE FIGURES

The foregoing and other objects of the present disclosure, the various features thereof, as well as the invention itself may be more fully understood from the following description, when read together with the accompanying drawings in which:

FIG. 1C is a scatter plot showing characteristic T reg markers in the population of donor mononuclear cells which are $CD127^{low}$;

FIG. 2A is a scatter plot showing characteristic T reg markers in the population of donor $CD4^+$ T cells which are $CD25^+$;

FIG. 2B is a scatter plot showing characteristic T reg markers in the population of donor $CD4^+$ T cells which are $Foxp3^+$;

FIG. 2C is a scatter plot showing characteristic T reg markers in the population of donor $CD4^+$ T cells which are $CD127^{low}$;

FIG. 9 is a graphic representation showing the inverse relationship between the level of T reg cells in the peripheral blood of relapsing-remitting MS patients and the duration of the disease.

DETAILED DESCRIPTION

Figure 1B:
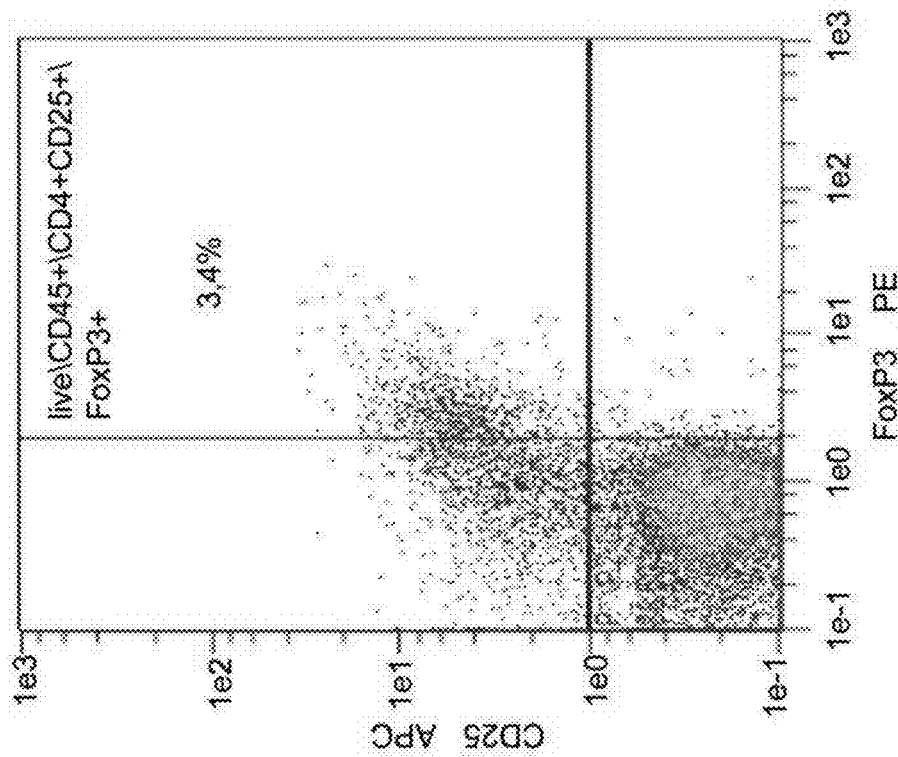
FIG. 1B is a scatter plot showing characteristic T reg markers in the population of donor mononuclear cells which are Foxp3.

Throughout this application, various patents, patent applications, and publications are referenced. The disclosures of these patents, patent applications, and publications in their entireties are hereby incorporated by reference into this application in order to more fully describe the state of the art as known to those skilled therein as of the date of the invention described and claimed herein. The instant disclosure will govern in the instance that there is any inconsistency between the patents, patent applications, and publications and this disclosure.

It has been discovered that the number of T reg cells in a patient suffering from relapsing-remitting MS is variable, and that there is an inverse relationship between the number of T reg cells in the peripheral blood of such patients and the degree of disability, severity, and duration of the condition. This was determined by studying both the degree of manifestation of the disease process and the number of T reg cells in the same group of patients in both the relapse stage and in the remission stage. Thus, a reduced level and functional activity of T reg cells are now understood to play an important role in the progression of the disease. On this basis, a promising method for treatment of MS was developed which includes the immune correction therapy comprising T reg cells. In addition, it has been determined that treatment with autologous T reg cells can inhibit the activity of autoimmune, autologous, cytotoxic T and B cells in a patient suffering from relapsing-remitting MS.

Definitions

For convenience, certain terms employed in the specification, examples, and appended claims are collected here. Unless defined otherwise, all technical and scientific terms used herein have the same meaning as commonly understood by one of ordinary skill in the art to which this invention belongs. The initial definition provided for a group or term herein applies to that group or term throughout the present specification individually or as part of another group, unless otherwise indicated.

The articles "a" and "an" are used herein to refer to one or to more than one (i.e., to at least one) of the grammatical object of the article. By way of example, "an element" means one element or more than one element.

The term "or" is used herein to mean, and is used interchangeably with, the term "and/or," unless context clearly indicates otherwise.

The term "about" is used herein to mean approximately, in the region of, roughly, or around. When the term "about" is used in conjunction with a numerical range, it modifies that range by extending the boundaries above and below the numerical values set forth. In general, the term "about" or "approximately" is used herein to modify a numerical value above and below the stated value by a variance of 20%.

As used herein, the term "T reg cells" refers to regulatory T cells with markers $CD4^+CD25^+Foxp3^+CD127^{low}$.

As used herein, the term "treating" refers to reducing or alleviating the symptoms, and/or preventing relapses and/or the progression of relapsing-remitting MS.

The term "preventing" refers to inhibiting or stopping a relapse in a person affected with relapsing-remitting MS.

The term "native" refers to cells from the body that have not been cultured, expanded, or treated with any compound other than a life-sustaining medium.

"Ex vivo-expanded" refers to native cells removed from the body and cultivated to proliferate. In the methods of the present disclosure, when cells treated in this way are returned to the body of the patient from which they were originally removed, they are referred to as "autologous, ex vivo-expanded cells".

As used herein, the term "healthy donor" refers to a mammal, such a human, of the same specie as the patient and who does not have any form of multiple sclerosis, does not have any blood-related disorder, and is considered by a physician to be in good health. The number of T reg cells in the blood of a healthy donor is used herein to determine the number of T reg cells that are administered to the patient.

2. Preparation of Autologous, Ex Vivo-Expanded T Reg Cells

Autologous T reg cells administered to a patient with relapsing-remitting MS according to the method of the disclosure are obtained from the peripheral blood of the patient. A sample of blood is removed and the fractionated to obtain a mononuclear cell (MNC) fraction from which the T reg cells are later isolated. The MNC fraction can be obtained from blood by any known method of blood fractiona-tion. For example, density gradient centrifugation, e.g. Ficoll-Hypaque density gradient centrifugation, can be used which takes advantage of the density differences between MNC's and other elements found in the blood sample. MNC's and platelets collect on top of the Ficoll-Hypaque layer because they have a lower density than red blood cells and granulocytes which collect at the bottom of the Ficoll-Hypaque layer.

To obtain T cells with a regulatory function, cells in this mononuclear fraction can be exposed to antibodies specific for CD4, as such T cells test positive for this marker. $CD4^+$ cells can then be separated from the MNC fraction, for example, using CD4 MicroBead columns (Myltenyi Biotec, Germany) exposed to a magnetic field. These $CD4^+$ cells are then screened for various other surface markers (CD25, Foxp3, and $CD127^{low}$) which are characteristic of T reg cells, for example, by antibody staining, as described above and in Example 1B below.

The selected T reg cells are then cultivated and expanded, ex vivo. For example, cultivation can be done by growing cells in a growth medium adapted for T cells (e.g., RMP1-1640) after the cells have been stimulated to proliferate (e.g., by exposure to allogenic, antigen-producing cells treated with mitomycin C, or TGF-β1 and IL-2).

To determine if the ex vivo-expanded T reg cells have comparable suppressor activity relative to the native cells (circulating in blood), these cells are tested for their ability to suppress the proliferation of certain target cells involved in the autoimmune process. This can be done using any assay involving contacting certain selected target cells (e.g., those in a mixed lymphocyte sample) with the expanded T reg cells, and measuring the target cell's ability to proliferate.

3. Pharmaceutical Formulation

To prepare the pharmaceutical composition, the ex vivo-expanded T reg cells having suppressor activity are suspended in a pharmaceutically acceptable carrier. This can be accomplished, e.g. by washing them twice in PBS, centrifuging them, and suspending the cell pellet in the carrier.

The phrase "pharmaceutically acceptable carrier" is employed herein to refer to liquid solutions which are, within the scope of sound medical judgment, suitable for use in contact with the live T reg cells without affecting their activity, and without being toxic to the tissues of human beings and animals or causing irritation, allergic response, or other complications, commensurate with a reasonable benefit/risk ratio. A useful pharmaceutically acceptable carrier may be an injectable solution which is biocompatible with the T reg cells and does not reduce their activity or cause their death.

Non-limiting examples of materials which can serve as pharmaceutically acceptable carriers include a solvent or dispersion medium containing, for example, sterile intravenous glucose/dextrose sugar solutions, Ringer's lactate or compound sodium lactate solution. Prevention of the action of microorganisms can be achieved by various antibacterial and antifungal agents, for example Clindamycin, Fluconazole, and/or Amphotericin B.

Sterile injectable solutions of expanded T reg cells can be prepared by incorporating the live cells in the required amount in an appropriate carrier.

The number of T reg cells which can be combined with a carrier material to produce a single-dosage form will vary depending upon the subject being treated, the particular mode of administration, the degree of MS symptoms, among others. Ultimately, the number of T reg cells in the pharmaceutical composition is that number that causes a therapeutic effect when administered to the patient. For example, the effective amount of the T reg cells may be about $1 \times 10^6$ to about $1.1 \times 10^7$ T reg cells/kg body weight, about $2 \times 10^6$ to about $8 \times 10^6$ T reg cells/kg body weight, about $4 \times 10^6$ to about $7 \times 10^6$ T reg cells/kg body weight, or about $5 \times 10^6$ to about $7 \times 10^6$ T reg cells/kg body weight.

4. Therapeutic Administration

Administration of the formulation containing the autologous T reg cells is useful to prevent or treat relapsing-remitting MS and/or to inhibit the activity of autoimmune, autologous, cytotoxic T and B cells in a patient suffering from relapsing-remitting MS. This step comprises administering a therapeutically effective amount of autologous T reg cells to the patient.

Methods of administration of the T reg cells in the pharmaceutical composition according to the disclosure described herein can be by any of a number of methods well known in the art. These methods include systemic or local administration by injection. Exemplary routes of administration include intravenous, intramuscular, intraperitoneal, or subcutaneous injection, and any combinations thereof.

The initial administering step may be a single administration or may comprise multiple administrations every 2 to 4 weeks after the initial administration. The initial administrating steps may be performed every 1 to 8 weeks. The number of initial administering steps at the start of treatment depends on the initial level of T reg cells in a patient's blood. The goal is to increase T reg cell number in the patient's blood until it is at the level of a healthy donor. This is determined by measuring the number of T reg cells in the blood of the patient before and after administering the T reg cells, and comparing that number to the number of T reg cells in a healthy patient. At the start of therapy, 1 to 8, 2 to 7, 3 to 6, 4 to 6, or 3 to 5 T reg cell injections can be administered every 2 to 4 or 3 to 4 weeks.

In addition, in some cases, an additional administering step may be performed every 3 to 6 months after the start of treatment, or at the end of the administration of the initial multiple treatments. However, a physician may determine that administration of the autologous T reg cells may be daily, weekly, or monthly. Even a single bolus provided during the remission stage can significantly improve the patient's condition, which can be proven by EDSS.

In order to determine the number of T reg cells in patient's blood, a sample is taken for measurement. Any method that enables the measurement of the number of T reg cells can be used. For example, the flow cytometry analysis can be performed. Measurement of the number of T reg cells can be done before and after each initial and secondary administering step(s), and further, can be done months after the initial; and any secondary administering step(s), for example, every two months.

The T reg cell-containing pharmaceutical composition can also be administered as part of a combination therapy with other agents to treat MS. "Combination therapy" refers to any form of administration combining two or more different therapeutic compounds, where the second compound is administered while the previously administered T reg cells are still effective in the body (e.g., the two therapeutics are simultaneously effective in the patient, which may include synergistic effects of the two compounds). For example, the different therapeutic compounds can be administered in separate formulations, either simultaneously or sequentially. Thus, a patient who receives such treatment can have a combined (conjoint) effect of different therapeutic compounds.

The following examples provide specific exemplary methods of the invention, and are not to be construed as limiting the invention to their content.

EXAMPLES

Example 1

Isolation and Ex Vivo-Expansion of $CD4^+CD25^+Foxp3^+CD127^{low}$ T Reg Cells

All the manipulations are performed under aseptic conditions in a Laminar Flow Class II Biosafety Cabinet which is located in a sterile clean room following to GMP regulations.

A. Blood Drawing

Peripheral blood (40 ml-50 ml) was taken from the ulnar vein of patients and placed into sterile tubes supplemented either with heparin or with $K_2$-EDTA (Vacutainer, BD, USA). 20 ml-30 ml blood (Vacutainer glass serum tubes) was kept at room temperature (RT) for 2 hours, and then centrifuged at 580 g for 10 min. The supernatant was collected into sterile tubes (Falcon, 15 ml conical tubes), which were incubated for 40 min at 56° C. to inactivate complement. The serum was bottled in 1.5 ml vials (Corning, USA) and frozen at −20° C.

B. Isolation of MNC's

The blood was transferred from tubes with the anticoagulant into 50 ml tubes, diluted 1:1 with Phosphate-buffered Saline (PBS, $Ca^{2+}Mg^{2+}$free, Gibco, United Kingdom). In order to separate lymphocytes, 35 ml MNC suspension was layered over 15 ml of a gradient solution (LimphoSep, d=1.077 g/ml, MP Biomedicals, USA) in 50 ml conical tubes (Falcon, USA). The tubes were centrifuged at 400 g for 30 min at 20° C. The upper layer was aspirated off, leaving the MNC layer, which was transferred to new 50 ml conical tubes. The tubes were filled with buffer and centrifuged at 300 g for 10 min. The cell pellet was resuspended in 50 ml PBS, combined in one tube, and then centrifuged at 300 g, 20° C. for 10 min. This procedure was repeated, and the cell pellet was resuspended in an appropriate amount of buffer.

For an estimation of initial $CD4^+CD25^+Foxp3^+CD127^{low}$ T reg cell numbers, the MNC population was stained with anti-$CD4^+$, anti-$CD25^+$, anti-$Foxp3^+$, and anti-$CD127^+$mAbs (Miltenyi Biotec, Germany; eBioscience, USA). The cells were detected by flow cytometry using a MACsQuant (Miltenyi Biotec, Germany).

Figure 1A:
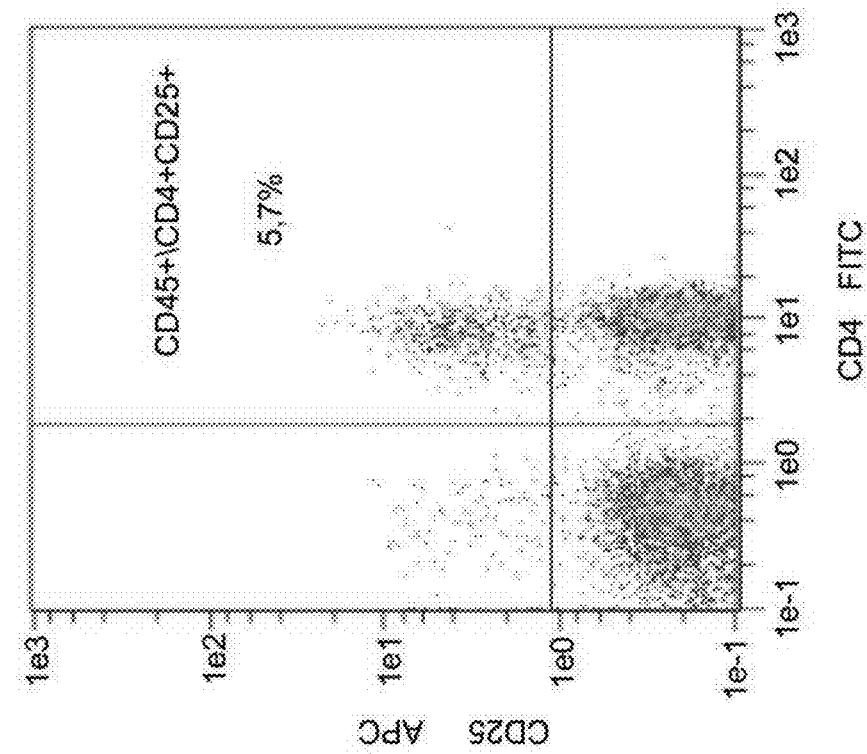
FIG. 1A is a scatter plot showing characteristic T reg markers in the population of donor mononuclear cells which are $CD25^+$.

FIGS. 1A-1C show a representative example of characteristic T reg cell markers in the donor's MNCs: 5.7% of $CD4^+$T cells co-expressed $CD25^+$(FIG. 1A); 3.4% of $CD4^+$T cells co-expressed Foxp3 (FIG. 1B); and 3.8% of CD4$^+$T cells co-expressed CD127$^{low}$ (FIG. 1C).

C. Isolation of CD4$^+$T Cells

In order to isolate CD4$^+$T cells, MNC were magnetically labeled with CD4$^+$mAbs according to the MACS Miltenyi Biotec (Germany) procedure. The immune phenotype of isolated CD4$^+$T cells was estimated by flow cytometry. In average, 94±4% (n=19) of the isolated cells were CD4$^+$T cells.

Expression of T cell markers on these cells is shown in FIGS. 2A-2C from one representative experiment (total 19): 97.5% of cells expressed CD4$^+$, and 12.6% of these CD4$^+$ cells co-expressed CD25$^+$(FIG. 2A); 6.3% of these CD4$^+$ cells co-expressed Foxp3$^+$(FIG. 2B); and 7.2% of these CD4$^+$ cells co-expressed CD127$^{low}$ (FIG. 2C).

D. Expansion of CD4$^+$CD25$^+$Foxp3$^+$CD127$^{low}$ T Reg Cells

The medium used for the T reg cell culture was RPMI-1640 which contains phenol red, L-glutamine, and 25 mM HEPES (Gibco, UK) with the addition of both 5-10% autologous serum and 1% pen/strep (Gibco, UK). This medium was supplemented with 1 ng/ml-50 ng/ml transforming growth factor β1 (TGFβ1) (R&D Systems, UK), 10 U/ml-1000 U/ml interleukin-2, (IL-2, R&D Systems, UK), 0.1 μg/ml-10 μg/ml mouse anti-human CD3 mAbs (Med biospecter, RF), and 0.1 μg/ml-10 μg/ml mouse anti-human CD28 mAbs (BD Pharmingen, USA). Expanded CD4$^+$T cells were cultured at 37° C. in 5% CO$_2$ for 6 to 8 days in flasks (either 25 cm$^2$ or 75 cm$^2$) with all supplements. After 3 to 4 days, IL-2, TGFβ1, anti-human CD3 mAbs, and anti-human CD28 mAbs were added.

E. Phenotypic Characterizations of T Reg Cells After Expansion In Vitro

Expanded cells were characterized at the end of culture. Flow cytometry was used to estimate the total numbers of live cells and the proportion of CD4$^+$CD25$^+$Foxp3$^+$CD127$^{low}$ cells in the cell suspension. To assure that the endotoxin levels in cell preparations were negligible, aliquots were tested with the Limulus assay kit (Sigma-Aldrich, USA), according to the manufacturer's protocols.

Table 1 shows the results of flow cytometry of initial CD4$^+$T cells and the same cells after 6 to 7 days of culture with stimulating molecules.

TABLE 1

| Markers | Marker Measurement in Initial cells | Marker Measurement in Expanded cells |
|---|---|---|
| CD4$^+$ | 93.9 ± 4.5 | 99.8 ± 0.2 |
| CD4$^+$CD25$^{hi}$ | 15.7 ± 4.0 | 95.9 ± 2.4 |
| CD4$^+$CD25$^+$CD62L$^+$ | 18.8 ± 9.0 | 54.6 ± 3.8 |
| CD4$^+$CD25$^+$Foxp3$^+$ | 6.1 ± 4.8 | 89.6 ± 3.2 |
| CD4$^+$CD25$^+$CD152$^+$ | 5.4 ± 2.7 | 93.8 ± 3.0 |
| CD4$^+$CD25$^+$CD127$^{low}$ | 6.7 ± 4.1 | 91.3 ± 3.2 |

Figure 3B:
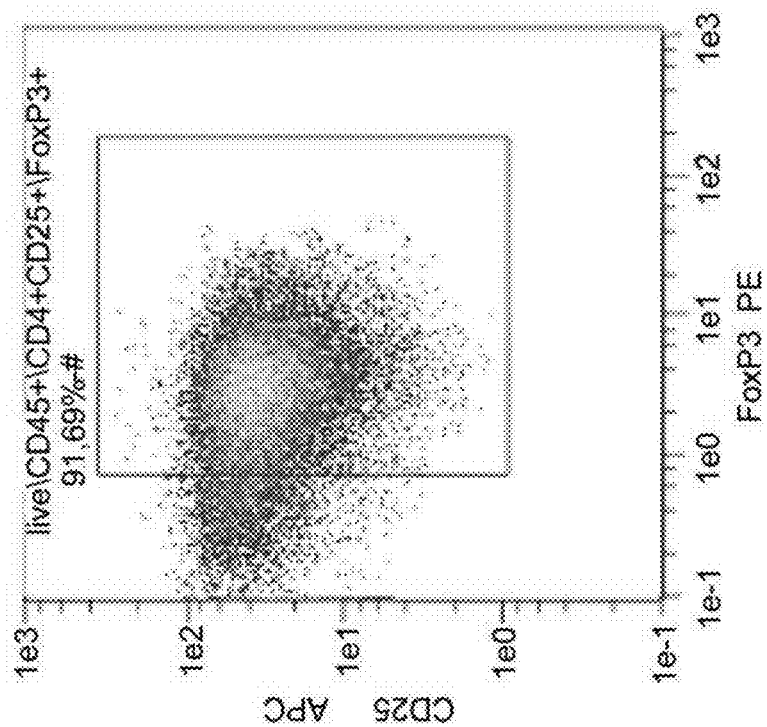
FIG. 3B is a scatter plot showing the expression of $Foxp3^+$ on T cells after 6 days of cultivation.
Figure 3A:
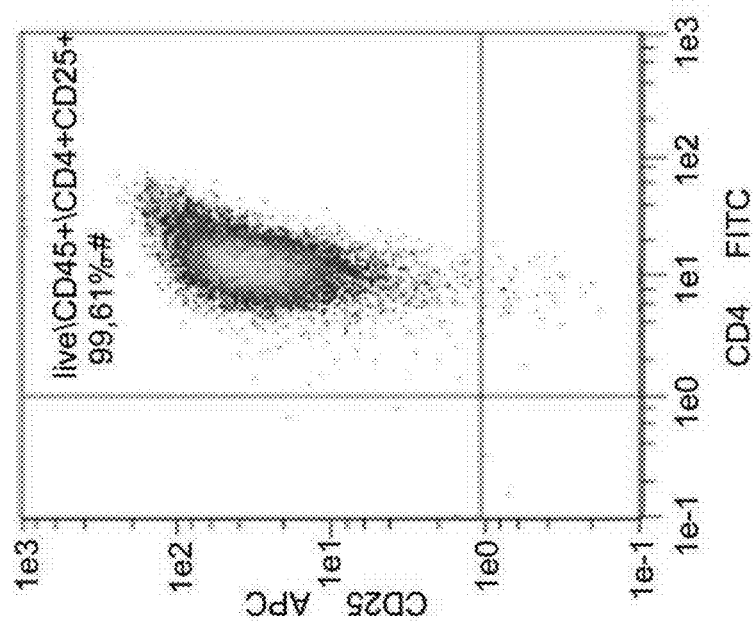
FIG. 3A is a scatter plot showing the expression of CD25hi on T cells after 6 days of cultivation.
Figure 3C:
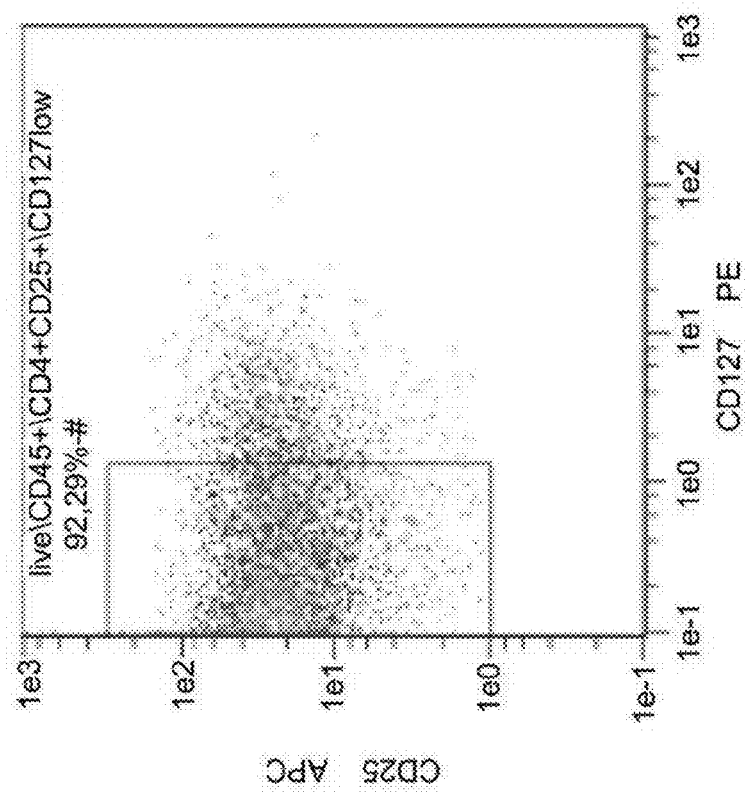
FIG. 3C is a scatter plot showing the expression of $CD127^{low}$ on T cells after 6 days of cultivation.

FIGS. 3A-3C show a representative sample of T reg cells expression after 6 days of in vitro culture. 99.6% CD4$^+$T cells co-expressed CD25$^{hi}$ (FIG. 3A); 91.7% CD4$^+$T cells co-expressed Foxp3 (FIG. 3B); and 92.3% CD4$^+$cells co-expressed CD127$^{low}$ (FIG. 3C).

Figure 4:
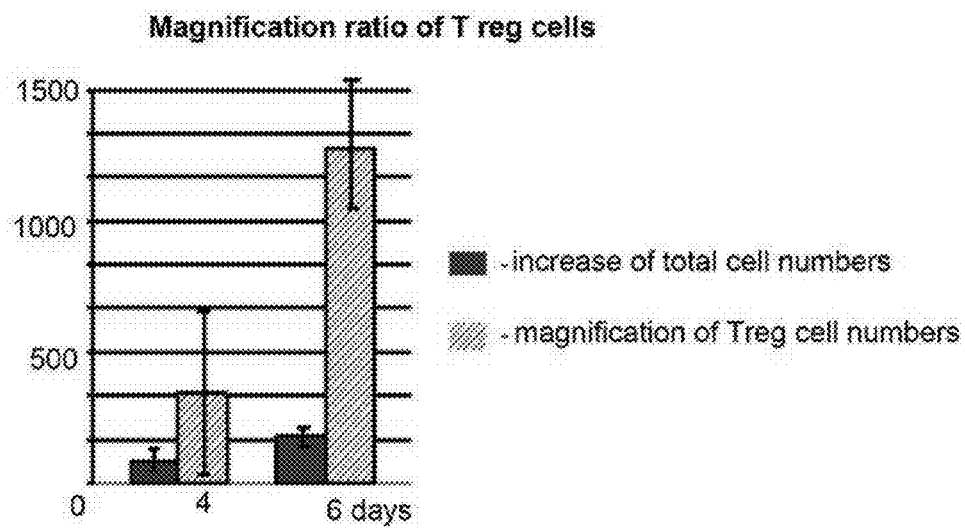
FIG. 4 is a graphic representation showing the increase in total number of cells (gray columns) and the increase in the number of T reg cells (shaded columns) at different stages of cultivation.

During the 6 days of propagating CD4$^+$T cells (obtained from 19 donors), the total amount of cells increased 27.2±7.3 X, whereas the number of T reg cells CD4$^+$CD25$^+$Foxp3$^+$ increased 1272±470 X (FIG. 4).

F. Functional Capacity of Expanded T Reg Cells

To determine if in vivo-expanded T reg cells keep their own suppressive ability, their suppressive capacity to inhibit proliferation of target cells in a mixed lymphocyte reaction (MLR) was compared initially and after the expansion of T reg cells. To this end, autologous target cells (CD4$^+$, CD4$^+$CD25$^-$) were isolated using the magnetic beads selection method (Miltenyi Biotec), stained with carboxyfluorescein succinimidyl ester (CFSE, Fluka, USA), and cultivated with or without equal numbers (1:1) of native T reg cells isolated from human blood or induced, ex vivo-expanded T reg cells. Either T cells CD4$^+$CD25$^-$T cells or CD4$^+$T cells were stimulated by 5 μg/ml (CD3 mAbs and allogeneic MNC treated with mitomycin C and depleted of CD3$^+$T cells by the magnetic bead selection method (Miltenyi Biotec). After 4 to 5 days of culture, cell proliferation was estimated by measurement of a reduction of 5(6)-Carboxyfluorescein diacetate N-succinimidyl ester (CFSE) in proliferating cells.

Figure 5:
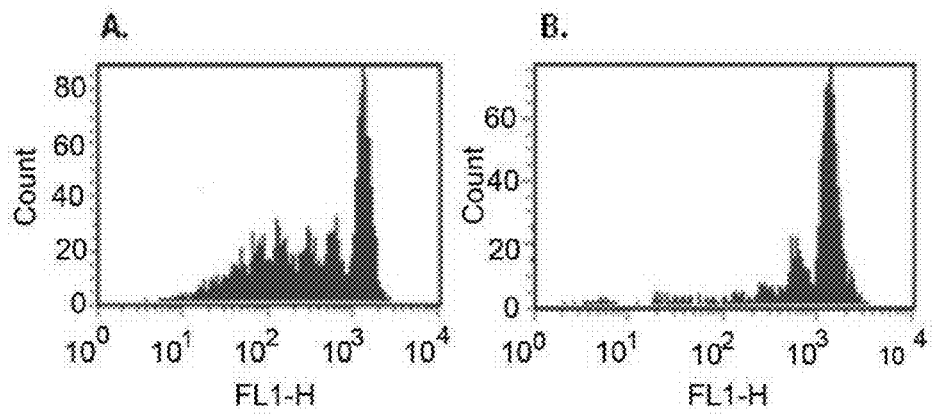
FIG. 5A is a graphic representation of the proliferation of target cells $CD4^+CD25^-$ in the absence of T reg cells.
FIG. 5B is a graphic representation of the proliferation of $CD4^+CD25^-$ cells in the presence of T reg cells.

The functional activity of T reg cells isolated from the peripheral blood of MS patients was found to be substantially reduced. FIGS. 5A-5B show the proliferation of target cells (CD4$^+$CD25$^-$) in the absence (FIG. 5A) and presence (FIG. 5B) of T reg cells.

Figure 6A:
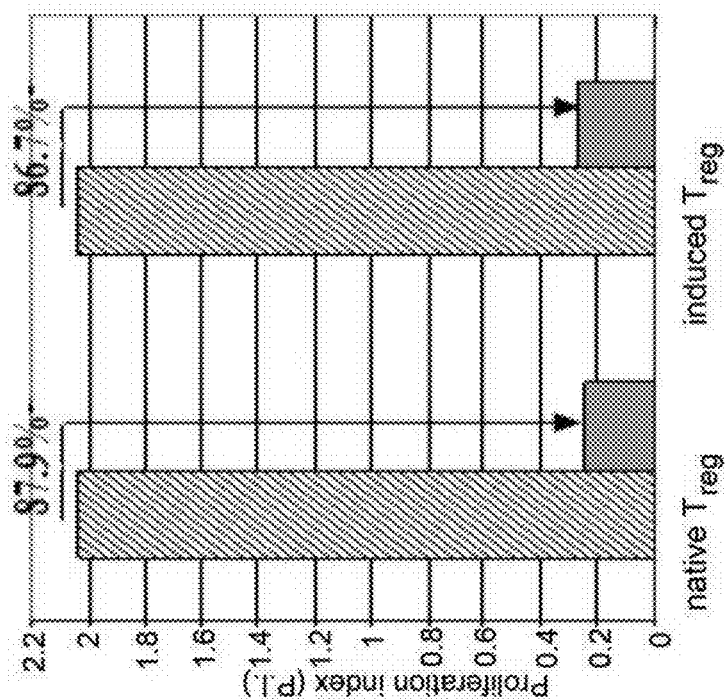
FIG. 6A is a graphic representation showing the inhibition of proliferation of $CD4^+$ T cells in the presence of native (cross-hatched) and expanded (shaded) T reg cells.
Figure 6B:
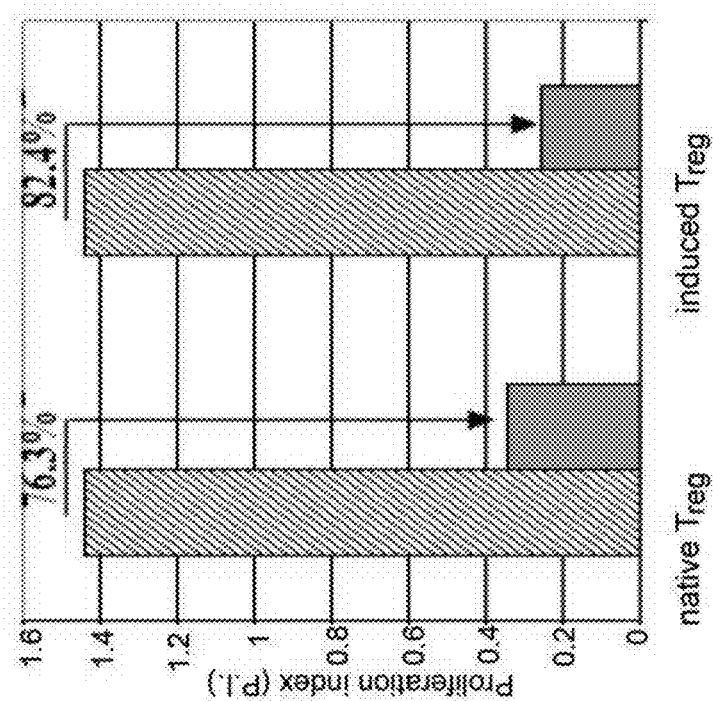
FIG. 6B is a graphic representation showing the inhibition of proliferation of $CD4^+CD25^-$ T cells in the presence of native (cross-hatched) and expanded (shaded) T reg cells.

FIGS. 6A-6B show the almost equal suppressive activity of both native and ex vivo-expanded T reg cells. Native T reg cells inhibited proliferation of 76.3% of CD4$^+$autologous target cells (FIG. 6A) and of 87.9% of CD4$^+$CD25$^-$autologous target cells (FIG. 6B). Correspondingly, induced T reg cells inhibited 82.4% of CD4$^+$target cells (FIG. 6A) and 86.7% of CD4$^+$CD25$^-$target cells (FIG. 6B).

It has been determined that the number of T reg cells in a patient suffering from relapsing-remitting MS is variable. This was determined by studying the immuno-phenotype of these cells within one group of patients in both the relapse stage.

Figure 7:
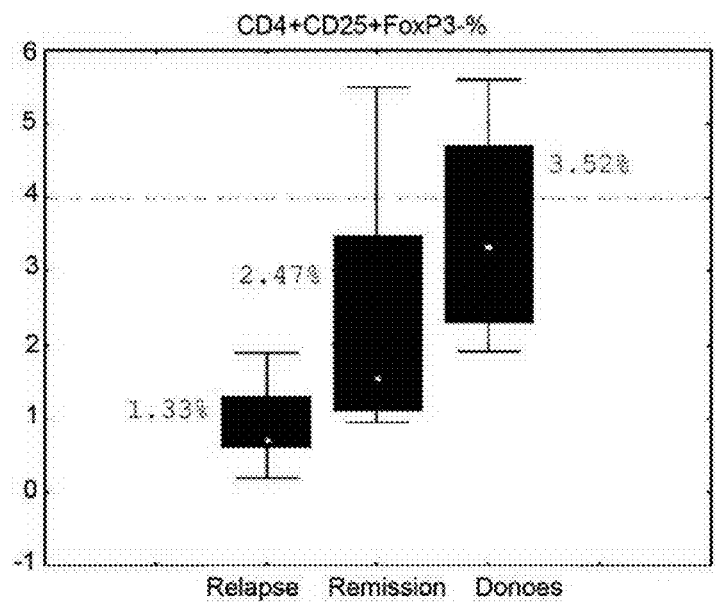
FIG. 7 is a graphic representation showing the level of T reg cells in the peripheral blood of relapsing-remitting MS patients in the relapse stage and in remission, compared to the levels in a healthy donor.

FIG. 7 shows the reduced number of T reg cells in the peripheral blood from patients in the relapse stage (1.33±0.95%); in the remission stage the number of T reg cells almost doubles (2.47±1.72), but remains below the healthy donors levels (3.52±1.37%).

Figure 8:
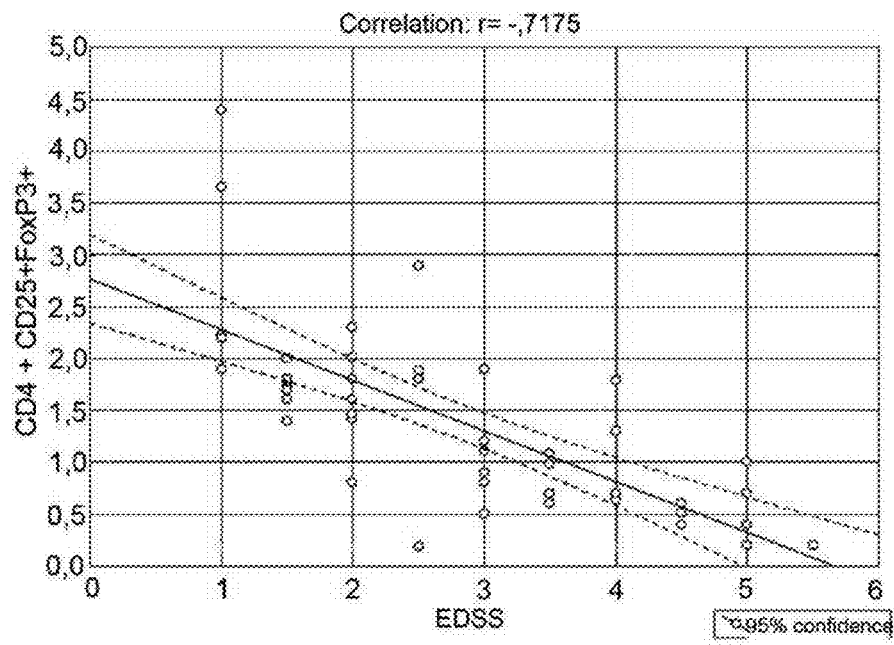
FIG. 8 is a graphic representation showing the inverse relationship between the level of T reg cells in peripheral blood of relapsing-remitting MS patients and the disease severity level according to the Expanded Disability Status Scale (EDSS)

FIG. 8 shows that there is an inverse relationship between the number of T reg cells and the severity of the disease, as determined by the EDSS.

FIG. 9 shows an inverse relationship between the number of T reg cells and duration of the disease. The T reg level of 1.97±0.9% was observed in patients who had the disease for less than 36 months, and in patients who had the disease for over 36 months, the T reg level was 0.73±0.4%. Thus, T reg cells play an important role in the progression of the disease.

On this basis, a promising method for treatment of MS is immune correction therapy comprising T reg cells.

Example 2

Treatment of MS Patients with T Reg Cells

Five patients with relapsing-remitting MS in the remission stage were treated with autologous, ex vivo-expanded CD4$^+$CD25$^+$Foxp3$^+$CD127$^{low}$ reg cells. Their pre-treatment neurological deficit was estimated according to EDSS scores shown in Table 2.

TABLE 2

| | | | | | Number of relapses | |
|---|---|---|---|---|---|---|
| Patients | Age | Sex | Duration of disease, months | EDSS | Total number | 12 months before administration of T reg cells |
| M. | 26 | F | 25 | 3.0 | 4 | 2 |
| T. | 33 | F | 47 | 2.5 | 5 | 3 |
| Z. | 29 | M | 27 | 3.0 | 4 | 2 |
| Ch. | 37 | F | 34 | 3.0 | 4 | 2 |
| P. | 29 | F | 29 | 2.5 | 5 | 3 |

Patients undergoing treatment did not receive either steroids or immunotherapy for at least 3 consecutive months. All the patients signed Consent Agreement before taking part in the study. The Protocol of the clinical study has been approved by the Board of Ethics of the Institution of Neurology of the Russian Academy of Medical Sciences.

Table 3 shows increased numbers of circulating T reg cells in patients 14 days after injection of autologous, ex vivo-expanded CD4$^+$CD25$^+$Foxp3$^+$T reg cells.

TABLE 3

| Patients | # of circulating T reg cells before treatment (% of positive cells) | # of T reg cells injected × $10^6$ | # of circulating T reg cells 2 weeks after injection (% of positive cells) |
| --- | --- | --- | --- |
| M. | 0.7 | 305 | 1.1 |
| T. | 0.7 | 400 | 1.5 |
| Z. | 0.4 | 273 | 1.1 |
| Ch | 0.4 | 250 | 1.4 |
| P. | 0.8 | 312 | 1.9 |

Table 4 shows the improved clinical status of the patients two weeks after the cell transplantation, as scored by EDSS.

TABLE 4

| | EDSS, scores | |
| --- | --- | --- |
| Patients | Before injection of T reg cells | 2 weeks after injection of T reg cells |
| M. | 3.0 | 2.0 |
| T. | 2.5 | 1.5 |
| Z. | 3.0 | 2.0 |
| Ch. | 3.0 | 2.0 |
| P. | 2.5 | 2.0 |

Average EDSS scores were 2.9±0.25 before injection of ex vivo-expanded T reg cells, and after injection, EDSS scores were reduced to 1.9±0.25.

The five treated patients were monitored for a year after treatment. Four of these patients showed no relapse, and one patient relapsed 9 months after the cell injection.

Table 5 shows the clinical manifestations in the patients treated as shown by the progression of demyelination (according to MRI) (before and after treatment).

TABLE 5

| Patients | Location of Demyelination (before treatment) | Location of Demyelination (1 yr. after treatment) |
| --- | --- | --- |
| M. | brain | no changes |
| T. | brain | no changes |
| Z. | brain and spinal cord | brain (3 new outbreaks) |
| Ch. | brain | no changes |
| P. | brain and spinal cord | no changes |

This data shows that treated patients showed minimal changes in demyelination after treatment, as determined by MRI.

These results obtained demonstrate that treatment with autologous, ex vivo-expanded T reg cells during the remission phase improved efficacy and reduced side effects of conventional treatment in patients with relapsing-remitting MS.

Example 3

Case Study In Vivo Treatment

A female patient "M," 26 years old, had first symptoms of the disease in 2006 in the form of leg cramps and numbness in her left hand finger tips. She displayed deterioration in the form of increasing dizziness, ingravescent weakness and numbness in the legs, gait instability, and delayed urination.

In August 2008, she was admitted to the hospital. The patient complained of numbness in her right hands and feet, weakness in the legs, unsteadiness when ambulating, and delayed urination. The brain MRI performed on Aug. 14, 2008, indicated demyelinating process. EDSS were estimated at 3. The patient received methyl-prednizolone pulse-therapy (total 5 g). The EDSS scores decreased to 1.5. The next deterioration was observed mid-February of 2009 and included numbness in the right arm and leg, increased weakness and stiffness in the legs, and gait deterioration. On Feb. 20, 2009 a brain MRI identified negative dynamics in the form of (the) emergence of new myelination hotbeds. EDSS scores increased to 3. The number of T reg cells CD4$^+$CD25$^+$Foxp3$^+$was determined by the flow cytometry analysis of the patient's blood cells on Mar. 12, 2009. The results are shown in Table 6.

TABLE 6

| Biomarker | % of positive cells |
| --- | --- |
| CD3 (T lymphocytes) | 73.2% |
| CD8 (cytotoxic T lymphocytes) | 33.2% |
| CD4 (helper T lymphocytes) | 55.5% |
| CD4$^+$CD25$^+$Foxp3$^+$ | 0.7% |
| CD4/CD8 ratio | 1.6 |
| CD19 (B lymphocytes) | 4.8% |
| CD16$^+$CD56 (NK cells) | 16.1% |

Flow cytometric analysis revealed a significant reduction in CD4$^+$CD25$^+$Foxp3$^+$T cells.

Harvesting of T reg cells was performed in 7 days after ex vivo expansion. During culture the numbers of CD4$^+$Foxp3$^+$T cells grew to 88.7%. The injection of 3.05×10$^8$ T reg cells in 2 ml of rheopolyglucin (Novofarm-Biosintez, Moscow, RF) was performed subcutaneously. Observation of the patient in the hospital during 2 weeks did not reveal any side effects after injection. Fourteen days after the injection of T reg cells, flow cytometry analysis (26 Mar. 2009) of the patient's blood demonstrated both elevated numbers of T reg cells and decrease of cytotoxic CD8$^+$T cells. The results are shown in Table 7.

TABLE 7

| Biomarker | % of positive cells |
| --- | --- |
| CD3 (T lymphocytes) | 74.1% |
| CD8 (cytotoxic T lymphocytes) | 22.6% |
| CD4 (helper T lymphocytes) | 53.4% |
| CD4$^+$CD25$^+$Foxp3$^+$ | 1.1% |
| CD4/CD8 ratio | 2.3 |
| CD19 (B lymphocytes) | 3.9% |
| CD16$^+$CD56 (NK cells) | 15.1% |

These results showed elevated (1.5×) numbers of CD4$^+$CD25$^+$Foxp3$^+$T reg cells in the patient's blood. However, the number of T reg cells did not reach the level found in normal donors' blood.

The patient was discharged from the hospital with the improvement of her status: regressed numbness in the right arm and leg, decreased weakness and stiffness in the legs, improved gait. EDSS scores went down to 2.

In summary, this treatment caused an elevation of circulating T reg cells, which can inhibit the activity of autoimmune $CD4^+$ and $CD8^+$ T cells. Injections of autologous T reg cells are useful for adjustment of imbalance in the immune system in patients with relapsing-remitting MS. Injections of T reg cells can be performed until the number of T reg cells in patient's blood reaches the level of healthy donors. This can be determined by assessment of the numbers of circulating T reg cells in the patient's blood every 3 to 4 months. Repeated injections of T reg cells can be performed to restore decreased levels of these cells.

Equivalents

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A pharmaceutical formulation comprising:
 a therapeutically effective amount of human, ex vivo-expanded, autologous regulatory $CD4^+CD25^+Foxp3^+$ $CD127^{low}$ T cells that have been treated with $\alpha CD3$ mAbs, $\alpha CD28$ mAbs, TGF-$\beta$1, and IL-2 (treated Treg cells) ; and
 a pharmaceutically acceptable carrier.

2. The formulation of claim 1, wherein the source of the Treg cells before treatment is the peripheral blood of a human.

3. The formulation of claim 2 wherein the treated Treg cells are present at $1\times10^6$ to $1.1\times10^7$ Treg cell/kg body weight of the human to be treated.

4. The formulation of claim 3, wherein the treated Treg cells are present at $2\times10^6$ to $8\times10^6$ Treg cells/kg body weight of the human to be treated.

5. The formulation of claim 3, wherein the treated Treg cells are present at $4\times10^6$ to $7\times10^6$ Treg cells/kg body weight of the human to be treated.

6. The formulation of claim 3, wherein the treated Treg cells are present at $5\times10^6$ to $7\times10^6$ Treg cells/kg body weight of the human to be treated.

7. The formulation of claim 1, wherein the carrier is an intravenous glucose/dextrose solution, Ringer's lactate solution, sodium lactate solution, or Rheopolyglukin.

8. The formulation of claim 1, further comprising another MS therapeutic compound.

* * * * *